United States Patent
Hsiung

(10) Patent No.: US 10,646,681 B2
(45) Date of Patent: May 12, 2020

(54) BUBBLE CONTINUOUS POSITIVE AIRWAY PRESSURE DEVICE

(71) Applicant: BESMED HEALTH BUSINESS CORP., New Taipei (TW)

(72) Inventor: Tao-Tsun Hsiung, New Taipei (TW)

(73) Assignee: Besmed Health Business Corp., New Taipei (TW)

( * ) Notice: Subject to any disclaimer, the term of this patent is extended or adjusted under 35 U.S.C. 154(b) by 386 days.

(21) Appl. No.: 15/598,577

(22) Filed: May 18, 2017

(65) Prior Publication Data

US 2018/0272097 A1 Sep. 27, 2018

(30) Foreign Application Priority Data

Mar. 24, 2017 (TW) .............................. 106109960 A

(51) Int. Cl.
*A61M 16/00* (2006.01)
*A61M 16/08* (2006.01)
(Continued)

(52) U.S. Cl.
CPC .... *A61M 16/0875* (2013.01); *A61M 16/0003* (2014.02); *A61M 16/0666* (2013.01);
(Continued)

(58) Field of Classification Search
CPC .. A61M 16/00; A61M 16/16; A61M 16/1045; A61M 16/0003; A61M 16/20–201; A61M 2205/3331; A61M 2205/3348; A61M 2205/3341; A61M 2240/00; B67D 7/08
See application file for complete search history.

(56) References Cited

U.S. PATENT DOCUMENTS 2,140,113 A * 12/1938 Gordon, Jr. ............. A61M 1/04
604/246
4,459,983 A 7/1984 Beyreuther et al.
(Continued)

OTHER PUBLICATIONS

"Snap-Fit Joints for Plastics", Bayer MaterialScience pp. 3,8 Archived 2012: https://web.archive.org/web/20121119232733/http://fab.cba.mit.edu/classes/S62.12/people/vernelle.noel/Plastic_Snap_fit_design.pdf (Year: 2012).*

*Primary Examiner* — Michael J Tsai
*Assistant Examiner* — Matthew Standard
(74) *Attorney, Agent, or Firm* — Rosenberg, Klein & Lee

(57) ABSTRACT

A bubble continuous positive airway pressure device has a container having an inner space, an inner conduit mounted in the inner space for conducting an airflow, an outer conduit mounted around the inner conduit, a rack longitudinally mounted on the outer conduit, a gear disposed in the inner space and meshed with the rack, and a knobt. The inner conduit has an aperture. The outer conduit is longitudinally slidable relative to the inner conduit, and has at least one through hole connected with the aperture. The knob drives the gear to rotate and the gear drives the rack, so as to drive the outer conduit to slide downward or upward in the inner space. The bubble continuous positive airway pressure device prevents dust and bacteria in the ambient environment from polluting the liquid in the container when adjusting gas pressure, so as to ensure the patients' health.

8 Claims, 10 Drawing Sheets

(51) Int. Cl.
*A61M 16/20* (2006.01)
*A61M 16/06* (2006.01)
*A61M 16/16* (2006.01)

(52) U.S. Cl.
CPC .... *A61M 16/0816* (2013.01); *A61M 16/0866* (2014.02); *A61M 16/16* (2013.01); *A61M 16/20* (2013.01); *A61M 16/201* (2014.02); *A61M 16/0672* (2014.02); *A61M 2205/3331* (2013.01); *A61M 2205/3348* (2013.01); *A61M 2240/00* (2013.01)

(56) References Cited

U.S. PATENT DOCUMENTS

| | | | |
|---|---|---|---|
| 6,805,120 B1 | 10/2004 | Jeffrey et al. | |
| 8,424,519 B2 * | 4/2013 | Loescher | A61M 16/00 128/203.16 |
| 9,108,008 B2 * | 8/2015 | Stenzler | A61M 16/201 |

* cited by examiner

BUBBLE CONTINUOUS POSITIVE AIRWAY PRESSURE DEVICE

CROSS-REFERENCE TO RELATED APPLICATION(S)

This application is based upon and claims priority under 35 U.S.C. 119(a) from Taiwan Patent Application No. 106109960 filed on Mar. 24, 2017, which is hereby specifically incorporated herein by this reference thereto.

BACKGROUND

1. Technical Field

The present invention relates to a bubble continuous positive airway pressure device, and more specifically to a bubble continuous positive airway pressure device connected to an artificial respiration system and regulates a gas pressure by passing the gas through the liquid contained in the bubble continuous positive airway pressure device so as to control the gas pressure inside the artificial respiration system.

2. Description of the Prior Art(s)

An artificial respiration system is usually used for assisting patients whose lungs are immature, such as preterm or newborn infants, to breathe. A gas pressure of an airflow flowing in the artificial respiration system is higher than an atmospheric pressure outside the artificial respiration system. The airflow delivers oxygen to the infant via an oxygen mask that covers the nose and mouth of the infant or via a nasal cannula. The gas pressure in the artificial respiration system is formed by a pressure adjusting device applying a resistant force to an end of a pipeline of the artificial respiration system.

With reference to FIG. 7, U.S. Pat. No. 4,459,983 discloses a pressure adjusting device for an artificial respiration system comprising a container 50, a tube 51, and an adjusting knob 52. Liquid is contained in the container 50. The tube 51 is inserted into the container 50. The top of the tube 51 is connected with the pipeline 53 of the artificial respiration system. The bottom of the tube 51 is dipped into the liquid. The length of the tube 51 immersed in the liquid may be adjusted by the adjusting knob 52. When the patient breathes, the airflow enters the tube 51 via the pipeline 53. By adjusting the depth of the tube 51 immersed in the liquid, the resistant force applied to the airflow varies so as to adjust the gas pressure in the pipeline 53.

With reference to FIG. 8, U.S. Pat. No. 6,805,120 provides a pressure adjusting device for an artificial respiration system comprising a container 60, a tube 61, and a height adjusting structure 62. Liquid is contained in the container 60. The tube 61 is inserted into the container 60. The height adjusting structure 62 comprises a protrusion and multiple annular grooves 621. The protrusion is disposed on the container 60. The protrusion is selectively combined with the annular grooves 621. The annular grooves 621 are disposed on the outer surface of the tube 61 at spaced intervals. When the patient breathes, the airflow enters the tube 61 via the pipeline. By combining the protrusion with one of the annular grooves from another, the depth of the tube 61 immersed in the liquid is adjusted so as to adjust the gas pressure in the pipeline.

With reference to FIGS. 9 and 10, U.S. Pat. No. 9,108,008 provides a pressure adjusting device for an artificial respiration system comprising a container 70, a tube 71, and a height adjusting structure 72. The container 70 comprises a hollowed outer casing 700 and a hollowed inner casing 701. The inner casing 701 is longitudinally inserted into the outer casing 700. The inner casing 701 comprises a bottom opening portion 702. The inside of the inner casing 701 is connected with the inside of the outer casing 700 via the bottom opening portion 702. Liquid is contained in the outer casing 700. The conduit 71 is longitudinally inserted into the inner casing 701. The lower end of the conduit 71 extends into the inside of the outer casing 700 and is dipped into the liquid. The height adjusting structure 72 comprises a locking member 720, an engaging member 721, a spiral groove 722, and multiple dimples 723. The locking member 720 is selectively combined with one of the dimples 723. The engaging member 721 is combined with the spiral groove 722. When the patient breathes, the airflow enters the conduit 71 via the pipeline. By adjusting the position of the engaging member 721 in the spiral groove 722 and combining the locking member 720 with one of the dimples 723 from another, the depth of the conduit 71 immersed in the liquid is adjusted so as to adjust the gas pressure in the pipeline.

However, to decrease the gas pressure in the pipeline by the conventional pressure adjusting devices mentioned above, the tubes 51, 61, and the inner casing 701 are moved upwardly, so that the outer surfaces of the tubes 51, 61 and the inner casing 701 are exposed to the ambient environment. In this way, to increase the gas pressure subsequently, the tubes 51, 61, and the inner casing 701 are moved downwardly and further dipped into the liquid. As such, the dust and the bacteria attached on the tubes 51, 61, and the inner casing 701 are prone to enter the liquid and pollute the liquid and endanger the patients' health.

To overcome the shortcomings, a bubble continuous positive airway pressure device to mitigate or obviate the aforementioned problems is provided.

SUMMARY

An objective of the present invention is to provide a bubble continuous positive airway pressure device to overcome the technical limitation in preventing dust and bacteria of the ambient environment from polluting the liquid in the container, so as to ensure the patients' health.

In accordance with an embodiment of the present invention, the bubble continuous positive airway pressure device comprises a container, an inner conduit for conducting an airflow, an outer conduit, a rack, a gear, and an knob. The container comprises a ventilation portion and an inner space. The inner conduit is longitudinally mounted in the inner space and comprises an aperture. The outer conduit is mounted around the inner conduit, is longitudinally slidable relative to the inner conduit, and comprises at least one through hole. The rack is longitudinally mounted on the outer conduit. The gear is disposed in the inner space and is meshed with the rack. The knob is disposed outside of the container. The aperture is connected to the at least one through hole, the knob drives the gear to rotate, and the gear drives the rack. When the gear drives the rack to move downward, the outer conduit slides downward in the inner space. When the gear drives the rack to move upward, the outer conduit slides upward in the inner space.

When in use, an adequate amount of liquid is contained in the container. The inner conduit is connected with the pipeline of the artificial respiration system. By adjusting the depth of the outer conduit immersed in the liquid, the gas pressure in the pipeline is adjusted. Since the outer conduit is mounted around the inner conduit and the inner conduit is disposed in the inner space, the outer conduit is not exposed to the ambient environment, and thus is not in contact with the dust and bacteria in the ambient environment. Hence, the bubble continuous positive airway pressure device prevents dust and bacteria in the ambient environment from polluting the liquid in the container when adjusting gas pressure, so as to ensure the patients' health.

In accordance with an embodiment, the container further comprises a cover, a base, a chamber, and a liquid room. The cover comprises a bottom opening portion. The base comprises a top opening portion combined with the bottom opening portion, so as to fix the cover and the base. The chamber is surrounded by the cover. The liquid room is surrounded by the base. In addition, the ventilation portion is disposed on the cover, and comprises a ventilation hole or a ventilation valve. The at least one through hole comprises multiple through holes.

In accordance with an embodiment, an outer thread is disposed on the bottom opening portion and an inner thread matched with the outer thread is disposed on the top opening portion, so as to combine the cover and the base by threading.

In accordance with an embodiment, the inner conduit further comprises a first end and a second end, and the aperture is disposed on the second end. The at least one through hole is disposed on a bottom of the outer conduit. An inner diameter of the outer conduit is equal to or larger than an outer diameter of the inner conduit. In addition, the bubble continuous positive airway pressure device further comprises a sealing member disposed between the second end of the inner conduit and the outer conduit.

In accordance with an embodiment, the bubble continuous positive airway pressure device further comprises a connecting conduit mounted through the container. The connecting conduit comprises an outer end and an inner end. The outer end protrudes outward from the container for mounting a joint to connect a pipeline of an artificial respiration system. Also, the inner conduit further comprises a first end connected with the inner end, and a second end. In addition, the inner conduit is connected to the pipeline of the artificial respiration system by the connecting conduit and the joint.

In accordance with an embodiment, the inner space contains a liquid, the outer conduit comprises a bottom dipped into the liquid, and a scale corresponding to a depth of the outer conduit immersed in the liquid is disposed on the knob. The airflow is conducted into the inner conduit from a pipeline of an artificial respiration system, and enters the liquid via the aperture and the at least one through hole, so as to produce bubbles. Besides, gases in the bubbles leave the inner space via the ventilation portion.

In accordance with an embodiment, the bubble continuous positive airway pressure device further comprises a connecting element formed as one piece with the gear and comprising a resilient buckle. The knob comprises a fastening recess fixed with the resilient buckle. Accordingly, the gear is connected with the knob by the connecting element.

In accordance with an embodiment, the bubble continuous positive airway pressure device further comprises a connecting element formed as one piece with the gear and comprising a fastening recess. The knob comprises a resilient buckle fixed with the fastening recess. Accordingly, the gear is connected with the knob by the connecting element.

In accordance with an embodiment, the inner conduit further comprises an outer surface, and the outer conduit further comprises an inner surface. The bubble continuous positive airway pressure device further comprises a sliding slot disposed in the outer surface and a sliding member disposed on the inner surface, so as to prevent the outer conduit and the inner conduit from rotating relative to each other.

In accordance with an embodiment, the inner conduit further comprises an outer surface, and the outer conduit further comprises an inner surface. The bubble continuous positive airway pressure device further comprises a sliding member disposed on the outer surface and a sliding slot disposed in the inner surface, so as to prevent the outer conduit and the inner conduit from rotating relative to each other.

Other objectives, advantages, and novel features of the embodiments of the present invention will become more apparent from the following detailed description when taken in conjunction with the accompanying drawings.

DETAILED DESCRIPTION

Figure 1:
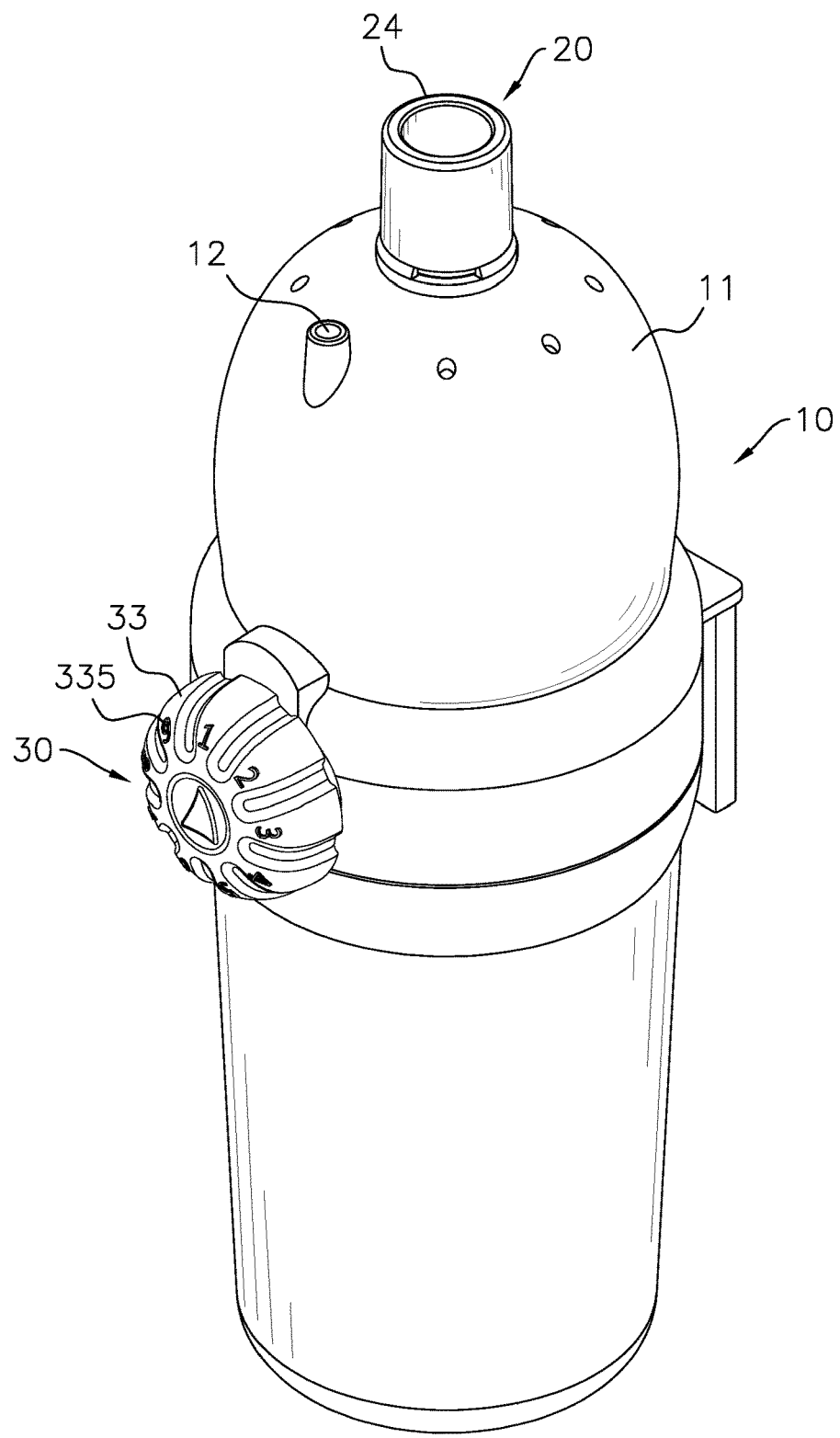
FIG. 1 is a perspective view of a bubble continuous positive airway pressure device in accordance with the present invention.
Figure 2:
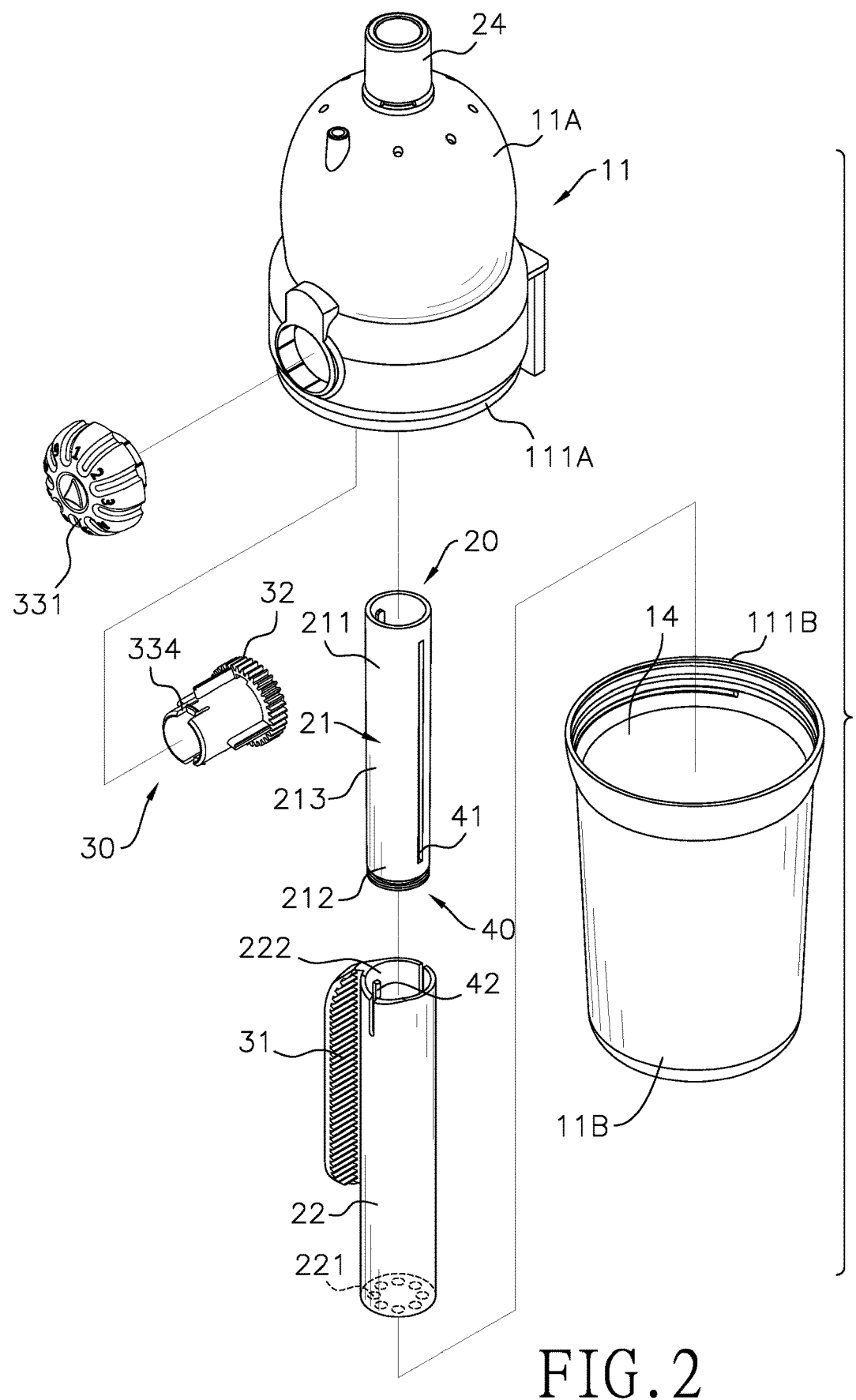
FIG. 2 is an exploded perspective view of the bubble continuous positive airway pressure device in accordance with the present invention.
Figure 3:
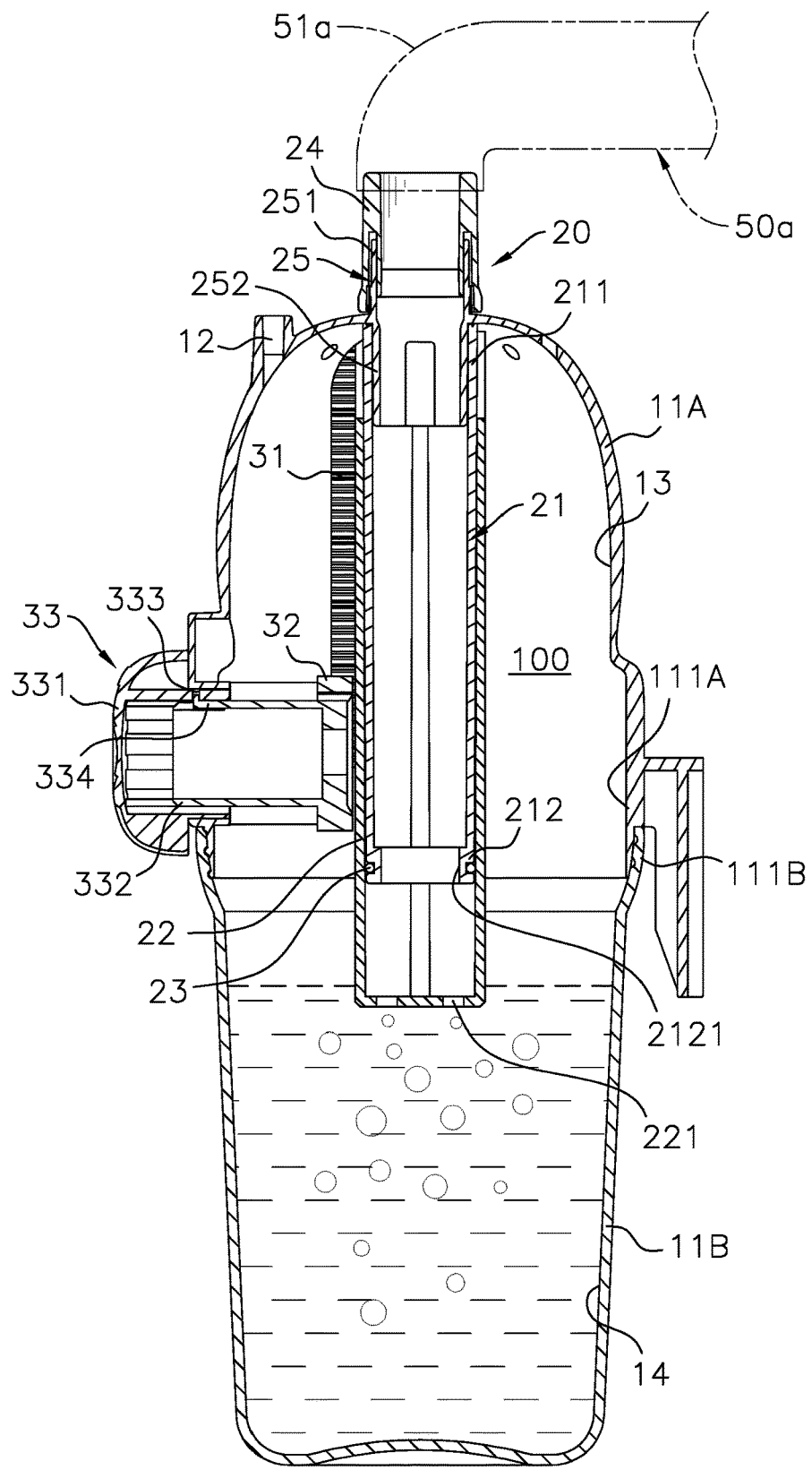
FIG. 3 is a first schematic view of a first operational state of the bubble continuous positive airway pressure device in accordance with the present invention.

With reference to FIGS. 1 to 3, a bubble continuous positive airway pressure device in accordance with the present invention comprises a container 10, a conduit assembly 20, and a height adjusting mechanism 30.

With reference to FIGS. 1 to 3, the container 10 comprises a casing 11 and an inner space 100. The inner space 100 is covered by the casing 11. In other words, the container 10 is hollowed. In addition, the container 10 comprises a ventilation portion. The ventilation portion may be a ventilation hole 12 or a ventilation valve. The ventilation hole 12 is formed through the casing 11 and is connected with the inner space 100.

With reference to FIGS. 1 to 3, in an embodiment, the container 10 comprises a cover 11A, a base 11B, a chamber 13, and a liquid room 14. The cover 11A and the base 11B constitute the casing 11. The cover 11A comprises a bottom opening portion 111A. The base 11B comprises a top opening portion 111B. The bottom opening portion 111A and the top opening portion 111B are combined to fix the cover 11A and the base 11B. The chamber 13 is surrounded by the cover 11A. The liquid room 14 is surrounded by the base 11B. The inner space 100 is constituted by the chamber 13 and the liquid room 14. The ventilation hole 12 is formed through the cover 11A. Specifically, the cover 11A and the base 11B are combined by threading. In an embodiment, an outer thread is disposed on, but not limited to, the bottom opening portion 111A, and an inner thread matched with the outer thread is disposed on, but not limited to, the top opening portion 111B.

With reference to FIGS. 1 to 3, the conduit assembly 20 is longitudinally mounted on the container 10. The conduit assembly 20 comprises an inner conduit 21 and an outer conduit 22. The inner conduit 21 is longitudinally disposed in the inner space 100, and comprises a first end 211 and a second end 212 opposite the first end 211. The first end 211 is connected to the casing 11. The second end 212 is disposed in the inner space 100 and comprises an aperture 2121. The outer conduit 22 is disposed in the chamber 13. The outer conduit 22 is mounted around the inner conduit 21 and is longitudinally slidable relative to the inner conduit 21. An inner diameter of the outer conduit 22 matches with an outer diameter of the inner conduit 21. In other words, the outer conduit 22 is longitudinally slidable relative to the inner conduit 21 in the inner space 100, and the inner diameter of the outer conduit 22 is equal to, or slightly larger than the outer diameter of the inner conduit 21. In addition, multiple through holes 221 connected with the aperture 2121 are disposed on the bottom of the outer conduit 22. Besides, a sealing member 23 is disposed between the second end 212 of the inner conduit 21 and the outer conduit 22, so as to enhance the sealing between the inner conduit 21 and the outer conduit 22.

With reference to FIGS. 1 to 3, in an embodiment, the conduit assembly 20 further comprises a joint 24 and a connecting conduit 25. The connecting conduit 25 is mounted through the casing 11. The connecting conduit 25 comprises an outer end 251 and an inner end 252. The outer end 251 protrudes outwardly from the casing 11. The joint 24 is mounted around the outer end 251. The first end 211 of the inner conduit 21 is mounted around the inner end 252, so as to connect to the casing 11 by the connecting conduit 25.

With reference to FIGS. 1 to 3, the height adjusting mechanism 30 controls the relative position of the outer conduit 22 and the inner conduit 21, so as to adjust the length of the outer conduit 22 extending into the liquid in the inner space 100, in other words, adjusting the depth of the outer conduit 22 immersed into the liquid.

With reference to FIGS. 1 to 3, in an embodiment, the height adjusting mechanism 30 comprises a rack 31, a gear 32, and an operating element 33. The rack 31 is longitudinally mounted on the outer conduit 22. The gear 32 is disposed in the inner space 100 and is meshed with the rack 31. The operating element 33 comprises a knob 331 and a connecting element 332. The connecting element 332 is columnar in shape. For instance, the connecting element is a connector tube. The gear 32 is connected with the knob 331 by the connecting element 332, which includes, but is not limit to: the connecting element 332 comprises a resilient buckle 334 and the connecting element 332 is combined with the knob 331 by the resilient buckle 334. The resilient buckle 334 is fixed with a fastening recess 333 of the knob 331. The gear 32 and the connecting element 332 are formed as one piece. In a variation of an embodiment, the knob 331 comprises a resilient buckle 334, and the knob 331 is combined with the connecting element 332 by the resilient buckle 334. The resilient buckle 334 is fixed with a fastening recess 333 of the connecting element 332.

With reference to FIG. 2, in an embodiment, the inner conduit 21 and the outer conduit 22 are cylindrical tubes. The bubble continuous positive airway pressure device further comprises a limiting structure 40. The limiting structure 40 is positioned between the inner conduit 21 and the outer conduit 22 for limiting the rotating angle of the outer conduit 22 relative to the inner conduit 21. Specifically, the limiting structure 40 is used for preventing the outer conduit 22 and the inner conduit from rotating relative to each other. The limiting structure 40 comprises a sliding slot 41 and a sliding member 42. The sliding member 42 is slidably disposed in the sliding slot 41. The inner conduit 21 comprises an outer surface 213. The outer conduit 22 comprises an inner surface 222. The sliding slot 41 is transversely recessed in the outer surface 213, and the sliding member 42 protrudes outwardly on the inner surface 222. In a variation of an embodiment, the sliding member 42 protrudes outwardly and longitudinally on the outer surface 213, and the sliding slot 41 is longitudinally recessed in the inner surface 222.

Figure 4:
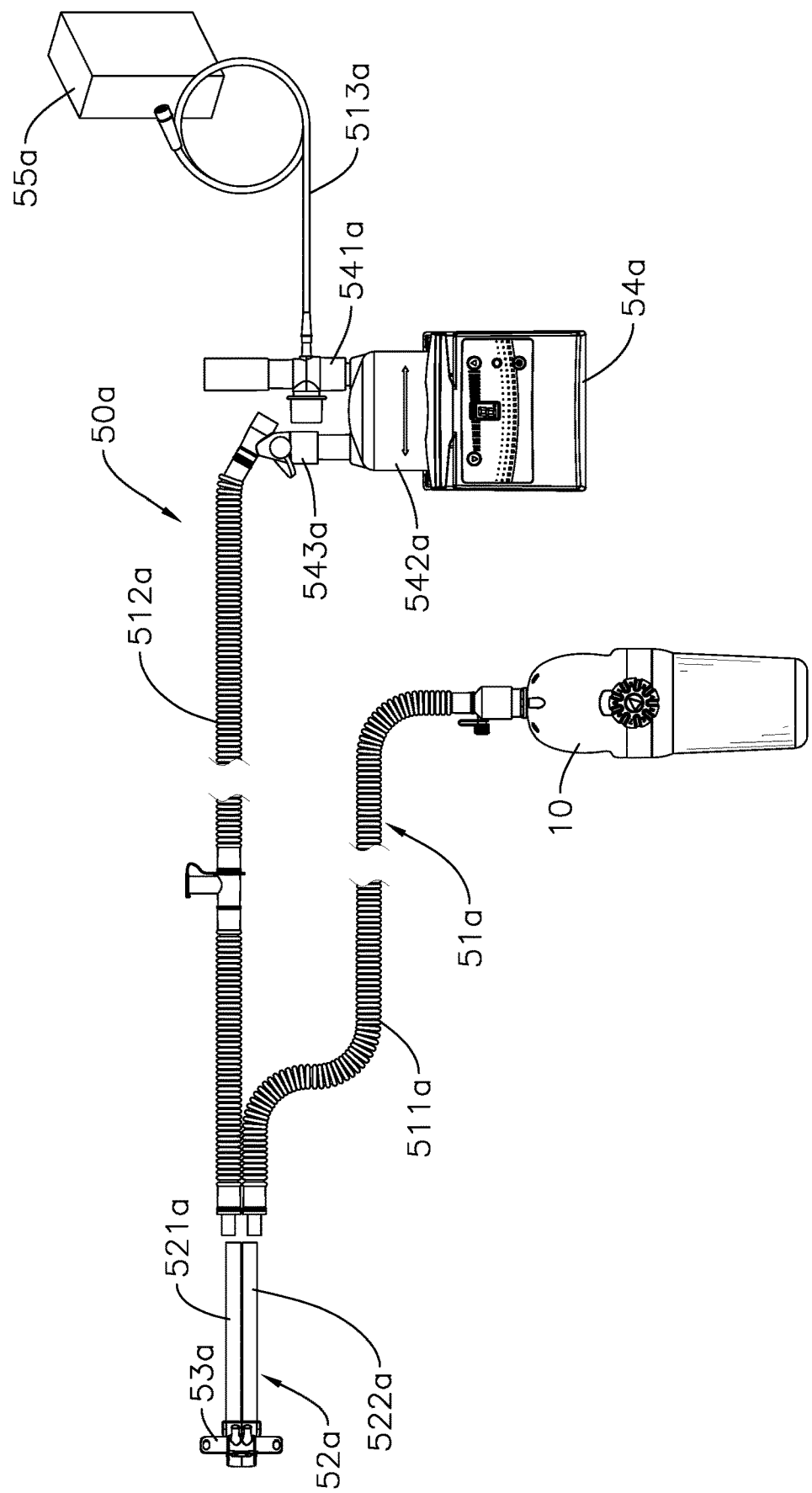
FIG. 4 is a schematic view for connecting an artificial respiration system with the bubble continuous positive airway pressure device in accordance with the present invention.

With reference to FIG. 4, the bubble continuous positive airway pressure device in accordance with the present invention is used with an artificial respiration system 50a. The artificial respiration system 50a comprises a pipeline 51a, a nasal adapter 52a, a nasal cannula 53a, a humidifier 54a, and a gas source 55a. The pipeline 51a comprises a first conduit 511a, a second conduit 512a, and a gas supply conduit 513a. The first conduit 511a is connected with the second conduit 512a via the nasal adapter 52a. The second conduit 512a is connected with the gas supply conduit 513a via the humidifier 54a. The gas supply conduit 513a is connected between the humidifier 54a and the gas source 55a. The nasal cannula 53a is connected with the nasal adapter 52a.

The bubble continuous positive airway pressure device in accordance with the present invention is connected with the first conduit 511a of the pipeline 51a in use. The gas source 55a supplies a gas to the gas supply conduit 513a. The gas is conducted into a humidifying room 542a of the humidifier 54a via an inlet 541a of the humidifier 54a and is humidified in the humidifying room 542a. Then the gas is conducted into the second conduit 512a via an outlet 543a of the humidifier 54a. After the gas is conducted into the first tube 521a of the nasal adapter 52a via the second conduit 512a, the gas is supplied to a patient via the nasal cannula 53a. An airflow formed by the gas may enter the first conduit 511a by the second tube 522a of the nasal cannula 53a and further enter the container 10. After the gas enters the container 10, the bubble continuous positive airway pressure device in accordance with the present invention applies a resistance to the gas, so as to keep the airflow in a continuous positive airway pressure.

Figure 5:
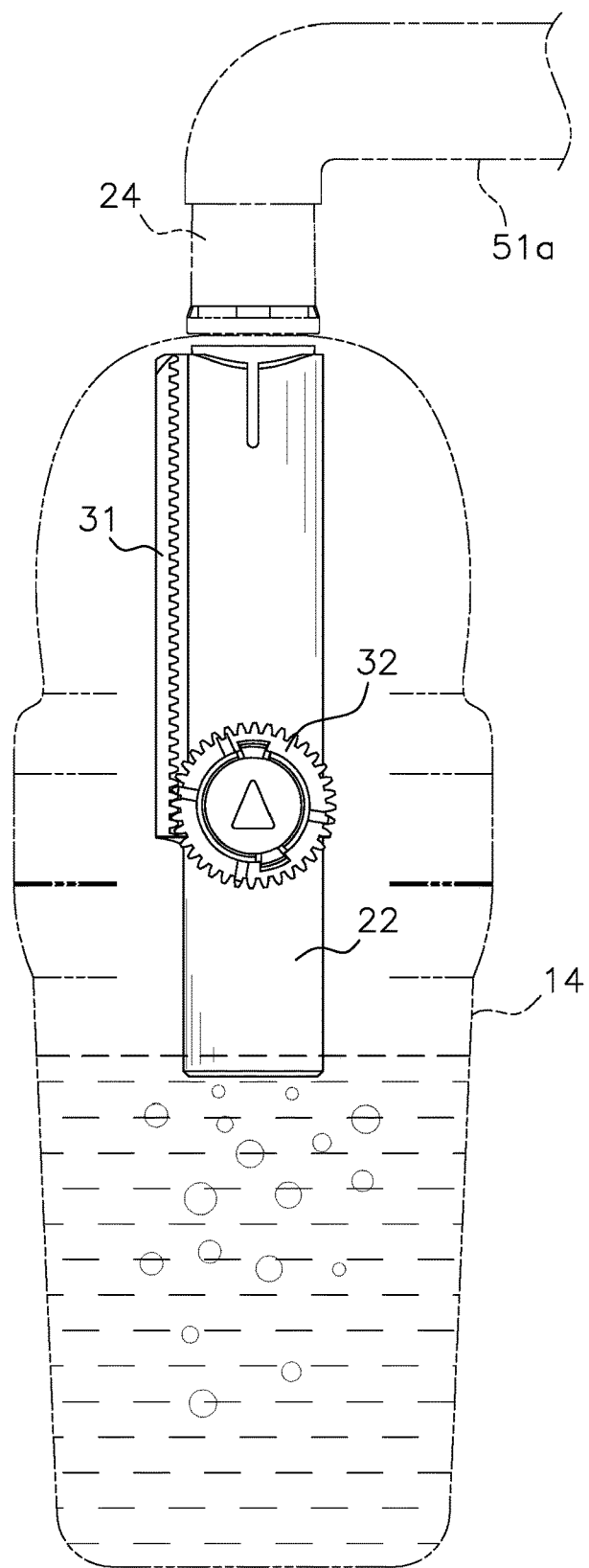
FIG. 5 is a second schematic view of the first operational state of the bubble continuous positive airway pressure device in accordance with the present invention.

With reference to FIGS. 3 to 5, specifically, the joint 24 is connected with the pipeline 51a of the artificial respiration system 50a, so that the inner conduit 21 is connected with the pipeline 51a by the connecting conduit 25 and the joint 24. Liquid is contained in the inner space 100 (liquid room 14). The bottom of the outer conduit 22 is dipped into the liquid. When the patient breathes, airflow enters the inner conduit 21 by the pipeline 51a and subsequently enters the liquid by the aperture 2121 and the through holes 221 to form bubbles. Afterwards, the air in the bubbles leaves the inner space 100 via the ventilation hole 12.

Figure 6:
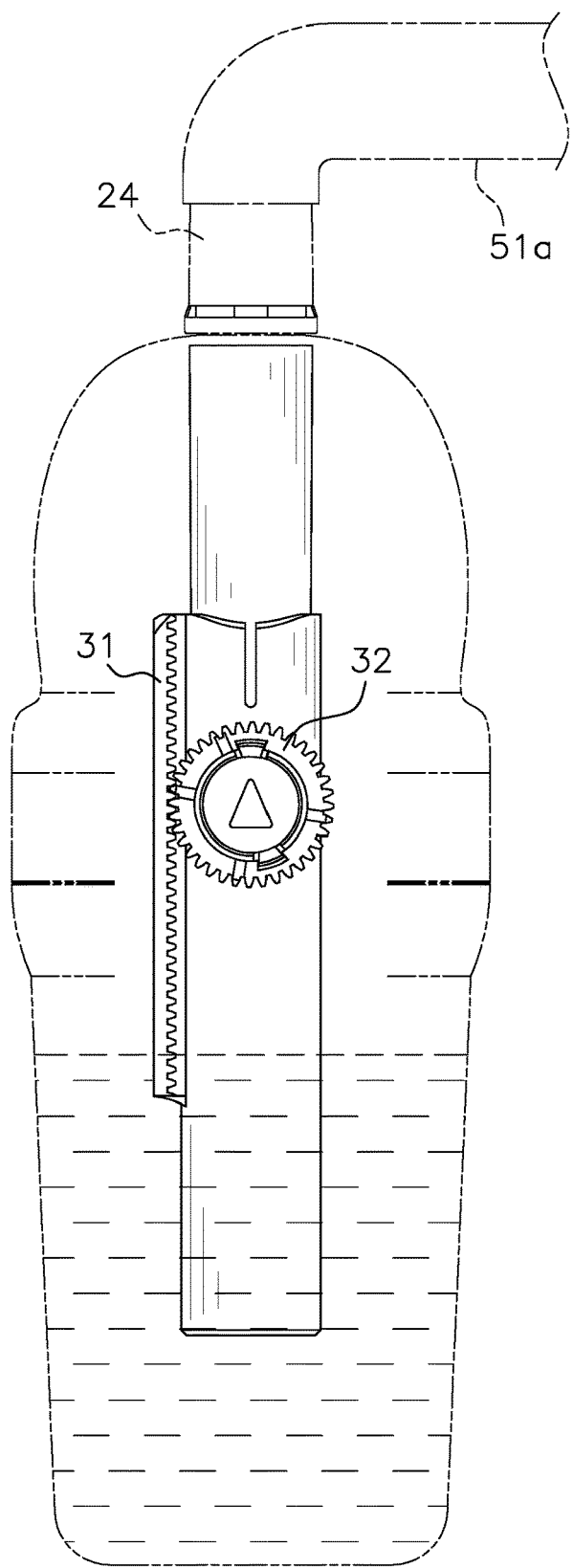
FIG. 6 is a schematic view of a second operational state of the bubble continuous positive airway pressure device in accordance with the present invention.
Figure 7:
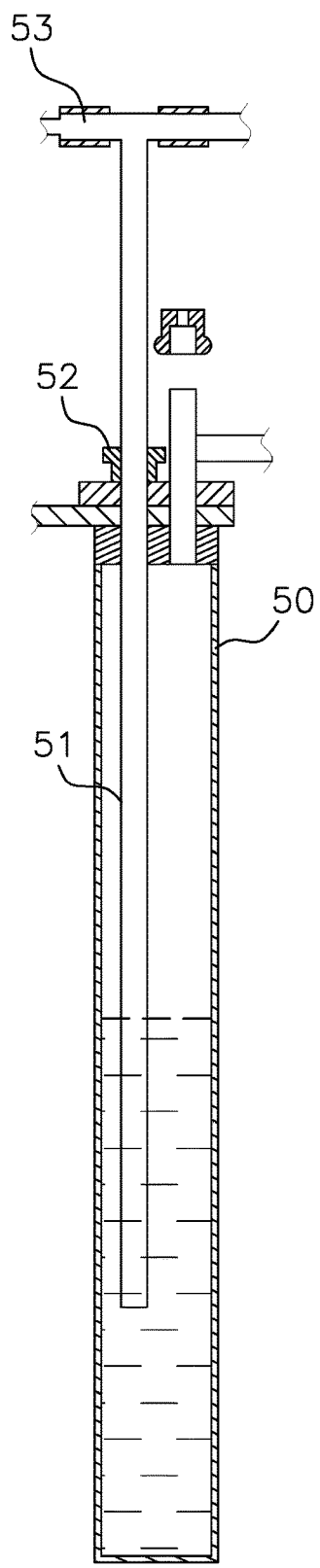
FIG. 7 is a schematic view of a pressure adjusting device for an artificial respiration system in accordance with the prior art.
Figure 8:
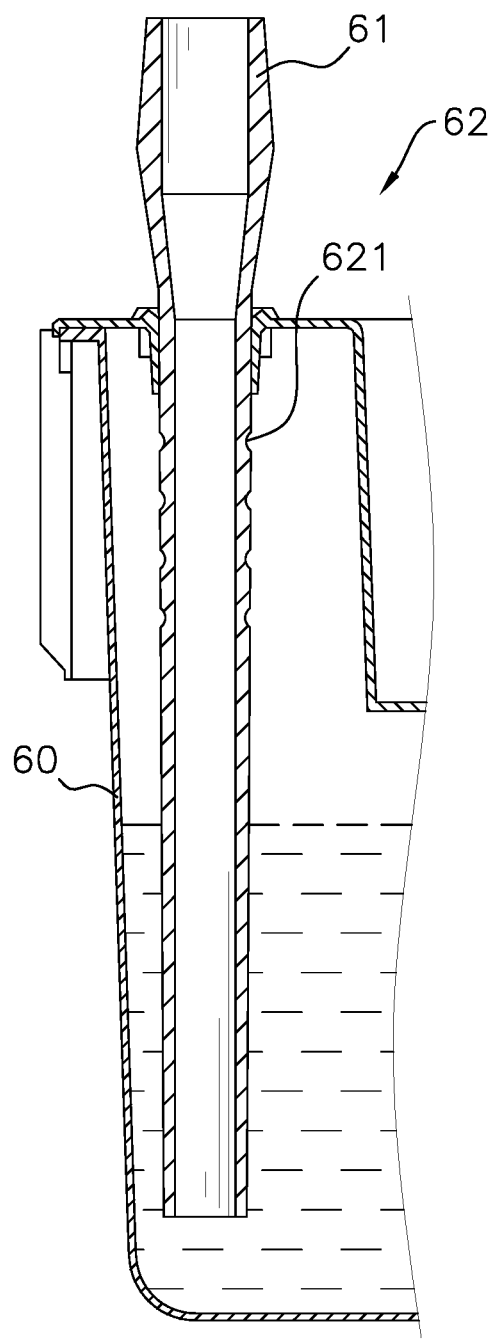
FIG. 8 is a schematic view of a pressure adjusting device for an artificial respiration system in accordance with the prior art.
Figure 9:
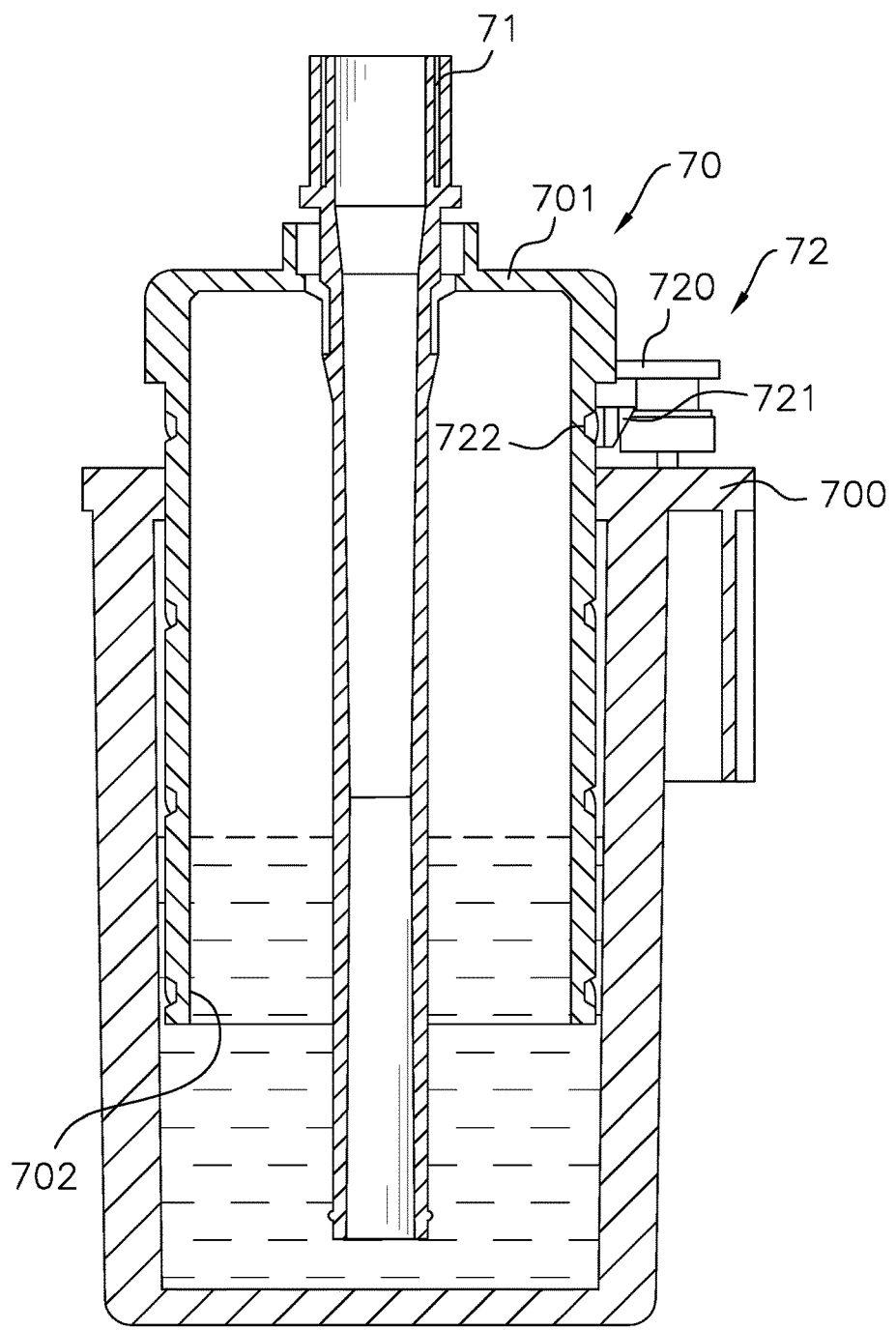
FIG. 9 is a schematic view of a pressure adjusting device for an artificial respiration system in accordance with the prior art.
Figure 10:
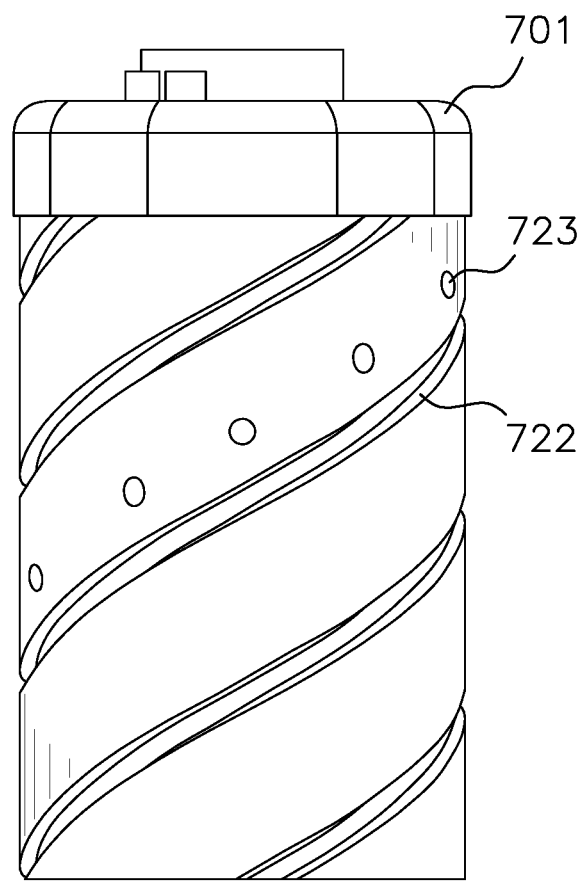
FIG. 10 is a side view of a container of the pressure adjusting device shown in FIG. 9.

With reference to FIGS. 3, 5 and 6, by rotating the operating element 33, the gear 32 rotates to drive the rack 31 to move downward or upward relative to the gear 32. Since the rack 31 is longitudinally mounted on the outer conduit 22, the outer conduit 22 moves downward relative to the inner conduit 21 in the inner space 100 and further dipped into the liquid in the inner space 100 when the gear 32 drives the rack 31 to move downward, thereby increasing the depth of the outer conduit 22 immersed in the liquid and increasing the gas pressure in the pipeline 51a. In another aspect, by rotating the operating element 33 to force the gear 32 to drive the rack 31 to move upward, the outer conduit 22 moves upward relative to the inner conduit 21 in the inner space 100. In this way, the depth of the outer conduit 22 immersed in the liquid is decreased and the gas pressure in the pipeline 51a is lowered.

With reference to FIGS. 2 and 3, a scale 335 corresponding to the depth of the outer conduit 22 immersed in the liquid is disposed on the knob 331, so that the gas pressure in the pipeline 51a is evaluated conveniently. Based on the above, the bubble continuous positive airway pressure device adjusts gas pressure in the pipeline 51a by adjusting the depth of the outer conduit 22 immersed in the liquid. Since the inner conduit 21 is disposed in the inner space 100 and the outer conduit 22 is mounted around the inner conduit 21, the outer conduit 22 slides relative to the inner conduit 22 in the inner space 100 during adjustment of the gas pressure in the pipeline 51a and is isolated from the ambient environment. Accordingly, the outer conduit 22 does not contact the dust and bacteria in the ambient environment. Therefore, the bubble continuous positive airway pressure device prevents dust and bacteria in the ambient environment from polluting the liquid in the container, thereby ensuring the patients' health.

What is claimed is:

1. A bubble continuous positive airway pressure device comprising:
   a container comprising a ventilation portion and an inner space;
   an inner conduit for conducting an airflow, the inner conduit longitudinally mounted entirely within the inner space and comprising an aperture;
   an outer conduit mounted around the inner conduit and contained within the inner space, being longitudinally slidable relative to the inner conduit, and comprising at least one through hole;
   a rack longitudinally mounted on the outer conduit;
   a gear disposed in the inner space and meshed with the rack; and
   a knob disposed outside of the container and coupled to the gear;
   wherein the at least one through hole is configured to pass the airflow entered from the aperture, the gear is configured to be rotatable by the knob, and the rack is configured to be driven by the gear;
   the outer conduit is configured to slide downward in the inner space by the gear driving the rack downward; and
   the outer conduit is configured to slide upward in the inner space by the gear driving the rack upward.

2. The bubble continuous positive airway pressure device as claimed in claim 1, wherein the container further comprises:
   a cover comprising a bottom opening portion;
   a base comprising a top opening portion combined with the bottom opening portion, so as to fix the cover and the base;
   a chamber surrounded by the cover; and
   a liquid room surrounded by the base;
   the ventilation portion is disposed on the cover, and comprises a ventilation hole or a ventilation valve; and
   the at least one through hole comprises multiple through holes.

3. The bubble continuous positive airway pressure device as claimed in claim 2, wherein an outer thread is disposed on the bottom opening portion and an inner thread matched with the outer thread is disposed on the top opening portion, so as to combine the cover and the base by threading.

4. The bubble continuous positive airway pressure device as claimed in claim 1, wherein the inner conduit further comprises a first end and a second end, and the aperture is disposed on the second end;
   the at least one through hole is disposed on a bottom of the outer conduit;
   an inner diameter of the outer conduit is equal to or larger than an outer diameter of the inner conduit; and
   the bubble continuous positive airway pressure device further comprises a sealing member disposed between the second end of the inner conduit and the outer conduit.

5. The bubble continuous positive airway pressure device as claimed in claim 1, wherein:
   the bubble continuous positive airway pressure device further comprises a connecting conduit mounted through the container, and the connecting conduit comprises:
   an outer end protruding outward from the container for mounting a joint to connect a pipeline of an artificial respiration system; and
   an inner end;
   the inner conduit further comprises:
   a first end connected with the inner end; and
   a second end; and
   the inner conduit is connected to the pipeline of the artificial respiration system by the connecting conduit and the joint.

6. The bubble continuous positive airway pressure device as claimed in claim 1, wherein:
   the inner space contains a liquid;
   the outer conduit comprises a bottom dipped into the liquid;
   a scale corresponding to a depth of the outer conduit immersed in the liquid is disposed on the knob;
   the inner conduit is configured to conduct the airflow from a pipeline of an artificial respiration system, the aperture is configured to conduct the airflow toward the through hole, and the through hole is configured to produce bubbles by the airflow entering the liquid; and
   the ventilation portion is configured to vent the bubble gases from the inner space.

7. The bubble continuous positive airway pressure device as claimed in claim 1, wherein:
   the bubble continuous positive airway pressure device further comprises a connecting element formed as one piece with the gear and comprising a resilient buckle;
   the knob comprises a fastening recess fixed with the resilient buckle; and
   the gear is connected with the knob by the connecting element.

8. The bubble continuous positive airway pressure device as claimed in claim 1, wherein:
- the inner conduit further comprises an outer surface;
- the outer conduit further comprises an inner surface; and
- the bubble continuous positive airway pressure device further comprises a sliding slot disposed in the outer surface and a sliding member disposed on the inner surface, so as to prevent the outer conduit and the inner conduit from rotating relative to each other.

* * * * *